United States Patent [19]

Nubel et al.

[11] Patent Number: 6,156,692
[45] Date of Patent: *Dec. 5, 2000

[54] RUTHENIUM-CONTAINING CATALYST COMPOSITION FOR OLEFIN METATHESIS

[75] Inventors: Philip O. Nubel; Craig Lane Hunt; David S. Choi, all of Naperville; Tobin J. Marks, Evanston, all of Ill.

[73] Assignee: BP Amoco Corporation, Chicago, Ill.

[*] Notice: This patent is subject to a terminal disclaimer.

[21] Appl. No.: 08/842,251

[22] Filed: Apr. 24, 1997

Related U.S. Application Data

[60] Provisional application No. 60/016,554, Apr. 30, 1996, and provisional application No. 60/033,257, Dec. 6, 1996.

[51] Int. Cl.[7] .................................................. B01J 31/00
[52] U.S. Cl. ........................ 502/155; 502/150; 502/152; 502/158; 502/169; 502/162
[58] Field of Search ................................... 502/150, 152, 502/155, 156, 158, 161, 169, 170, 172, 162

[56] References Cited

U.S. PATENT DOCUMENTS

| | | | |
|---|---|---|---|
| 3,117,952 | 1/1964 | Meriwether | 260/94.1 |
| 3,597,403 | 8/1971 | Ofstead | 260/88.2 |
| 3,798,175 | 3/1974 | Streck et al. | 252/429 |
| 3,855,323 | 12/1974 | Lyons | 260/666 A |
| 3,857,825 | 12/1974 | Streck et al. | 260/88.1 |
| 3,957,827 | 5/1976 | Lyons | 502/155 |
| 3,962,294 | 6/1976 | Lyons | 502/155 |
| 4,323,508 | 4/1982 | Herrington et al. | 260/346.11 |
| 5,312,940 | 5/1994 | Grubbs et al. | 556/136 |
| 5,324,616 | 6/1994 | Sacripante et al. | 430/137 |
| 5,342,909 | 8/1994 | Grubbs et al. | 556/136 |
| 5,405,924 | 4/1995 | Kelsey | 526/142 |
| 5,491,206 | 2/1996 | Brown-Wensley et al. | 526/126 |
| 5,559,262 | 9/1996 | Beatty et al. | 502/155 |
| 5,599,962 | 2/1997 | Beatty et al. | 556/21 |
| 5,710,298 | 1/1998 | Grubbs et al. | 502/155 |
| 5,726,334 | 3/1998 | Beatty et al. | 502/155 |
| 5,728,785 | 3/1998 | Grubbs et al. | 526/142 |
| 5,831,108 | 11/1998 | Grubbs et al. | 502/152 |
| 5,912,376 | 6/1999 | Van Der Schaaf et al. | 502/155 |
| 5,917,071 | 6/1999 | Grubbs et al. | 502/152 |
| 5,939,504 | 8/1999 | Woodson, Jr. et al. | 502/152 |
| 5,942,460 | 8/1999 | Garland et al. | 502/169 |
| 5,977,393 | 11/1999 | Grubbs et al. | 502/162 |
| 5,981,421 | 11/1999 | Paez et al. | 502/169 |
| 5,998,326 | 12/1999 | Hafner et al. | 502/155 |
| 6,043,380 | 3/2000 | Okeda et al. | 502/162 |
| 6,048,993 | 4/2000 | Grubbs et al. | 502/162 |
| 6,077,805 | 3/2000 | Van Der Schaaf et al. | 502/155 |

FOREIGN PATENT DOCUMENTS

| | | |
|---|---|---|
| 0 366 390 | 5/1990 | European Pat. Off. . |
| 0 839 821 | 10/1997 | European Pat. Off. . |
| WO 91/02588 | 3/1991 | WIPO . |
| WO 92/15400 | 9/1992 | WIPO . |
| WO 96/16100 | 5/1996 | WIPO . |
| WO 96/20235 | 7/1996 | WIPO . |
| WO 97/40934 | 11/1997 | WIPO . |
| WO 98/39346 | 9/1998 | WIPO . |

OTHER PUBLICATIONS

C. Grunwald et al., Advance ACS Abstracts, vol. 4, No. 6, p. 140, Mar. 15, 1996.
Gruenwald, C., et al., "Five–Coordinate 16–Electron Carbene– and Vinylidenruthenium (II) Complexes Prepared from [RuC12(C8H12)]n or from the New Dihydridoruthenium (IV) Compound [RuH2C12(PiPr3)2]", Organometallics (1996), 15: 1960–1962.
Demonceau, A., et al., Novel Ruthenium–Based Catalyst Systems for the Ring–Opening Metathesis Polymerization of Low–Strain Cyclic Olefins, Macromolecules (1997), 30: 3127–3136.
K.J. Ivin, "Summary of Catalyst Systems", Olefin Metathesis, Academic Press, New York, 1983, p. 34.
Porri, L., et al., "Ring–Opening Polymerizataion of Cycloolefins with Catalysts Derived from Ruthenium and Iridium", Die Makromolekulare Chemie, 1974, 175: 3097–3115.
Demonceau, A., et al., "Ruthenium–catalysed ring–opening metathesis polymerization of cycloolefins initiated by diazoesters", J. Mol. Catal, 1992, 76: 123–132.
Stumpf, A.W., et al., "Ruthenium–based Catalysts for the Ring Opening Metathesis Polymerization of Low–strain Cyclic Olefins and of Functionalised Derivatives of Norbornene and Cyclooctene", J. Chem. Soc., Commun., 1995, pp. 1127–1128.
Schwab, P., et al., A "Series of Well–Defined Metathesis Catalysts—Synthesis of [RuC12(=CHR')(PR3)2] and Its Reactions", Agnew. Chem. Int. Ed. Engl., 1995, 34: 2039–2041.
Schwab, P., et al., "Synthesis and Applications of RuC12(=CHR')(PR3)2: The Influence of the Alkylidene Moiety on Metathesis Activity", J. Am. Chem. Soc., 1996, 118: 100–110.
Creary, X., "Tosylhydrazone Salt Pyrolyses: Phenyldiazomethanes", Org. Synth., Coll. vol. 7, 1990, pp. 438–443.

*Primary Examiner*—Mark L. Bell
*Assistant Examiner*—J. Pasterczyk
*Attorney, Agent, or Firm*—James R. Henes; Stephen L. Hensley

[57] ABSTRACT

A ruthenium-containing metathesis catalyst system which contains a ruthenium compound (A), a phosphorus compound (B), and a compound (C) containing a carbon-to-carbon triple bond. The mole ratio of compounds A:B:C is typically in the range of about 1.0:0.01–100:0.01–100. The ruthenium compound (A) is a Ru(II), Ru(III), or Ru(IV) compound containing an anionic ligand (X) and optionally an arene ligand and optionally a phosphorus compound ligand. The phosphorus compound (B) is optional if the ruthenium compound (A) contains a phosphorus-containing ligand. The catalyst system is employed in processes to metathesize olefins, including ring-opening metathesis polymerization of cyclic olefins, metathesis of acyclic olefins, acyclic diene metathesis oligomerization or polymerization, cross-metathesis of cyclic and acyclic olefins, ring-closing metathesis, metathesis depolymerization of unsaturated polymers, and metathesis of functionalized olefins.

14 Claims, No Drawings

RUTHENIUM-CONTAINING CATALYST COMPOSITION FOR OLEFIN METATHESIS

REFERENCE TO RELATED APPLICATIONS

This application claims the benefits of U.S. Provisional Application Ser. No. 60/016,554, filed Apr. 30, 1996, and U.S. Provisional Application Ser. No. 60/033,257, filed Dec. 6, 1996, both of which are incorporated herein by reference in their entirety.

BACKGROUND OF THE INVENTION

This invention is directed to ruthenium-based catalyst systems for olefin metathesis and to catalytic olefin metathesis processes.

Conventional ring-opening olefin metathesis polymerization (ROMP) is the catalyzed reaction of a cyclic olefin monomer to yield an unsaturated polymer:

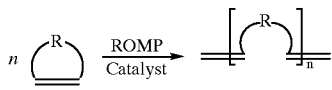

Procedures to prepare polymeric hydrocarbons having reactive functional endgroups have used cyclic olefinic compounds in conjunction with a ring opening step. Ofstead (U.S. Pat. No. 3,597,403) teaches a process for ring-opening polymerization of unsaturated alicyclic compounds, preferably unsaturated alicyclic compounds of a single unsaturated alicyclic ring, in the presence of a catalyst system comprising an alkylaluminum halide, molecular oxygen, and a compound of tungsten or molybdenum; generally the single unsaturated alicyclic ring contains at least four carbon atoms and not more than five carbon atoms wherein the carbon-to-carbon double bonds in the ring are not adjacent and are non-conjugated. Streck et al. (U.S. Pat. No. 3,798,175) teaches a process for ring opening polymerization of cyclic olefins and forming terminal carbalkoxy groups by employing a catalyst system consisting essentially of (1) a tungsten or molybdenum compound, (2) an organo aluminum compound, and (3) an unsaturated carboxylic acid ester. Streck et al. (U.S. Pat. No. 3,857,825) discloses a process for production of polymeric hydrocarbons having reactive silyl end groups by a ring-opening polymerization of a cyclic olefin in the presence of a catalytic amount of a halogenated compound of a metal selected from the group consisting of niobium, tantalum, molybdenum, tungsten and rhenium, and a halogen, alkoxy, carboxylate or Lewis acid.

Ruthenium-based catalysts for olefin metathesis have become of interest because they are able to effect the metathesis of certain types of olefins containing functional groups (e.g., hydroxyl, carboxylic acid, or ester groups), unlike many metathesis catalysts based on other metals such as molybdenum, tungsten, or rhenium. However, most ruthenium-based catalysts only can effect metathesis of highly strained cyclic olefins such as norbornene and norbornene derivatives, cyclobutene and cyclobutene derivatives, and dicyclopentadiene, and are unable to metathesize less strained cyclic olefins or acyclic olefins (K. J. Ivin, Olefin Metathesis, Academic Press, New York, 1983, p. 34). For example, $RuCl_3$ catalyzes the ring-opening metathesis polymerization (ROMP) of norbornene but not olefins with significantly lower ring strain such as cyclopentene, cyclooctene, or 1,5-cyclooctadiene. Porri et al. (L. Porri et al., Die Makromolekulare Chemie, 1974, 175: 3077–3115) reported two ruthenium compounds [dichloro (2,7-dimethylocta-2,6-diene-1,8-diyl)ruthenium and bis (trifluoroacetato)-2,7-dimethylocta-2,6-diene-1,8-diyl) ruthenium] that are able to cause slow metathesis of cyclopentene after treatment with hydrogen, but these systems were not able to effect metathesis of cyclooctene or acyclic olefins.

Recently, Noels et al. (A. Demonceau, A. F. Noels, E. Saive, and A. J. Hubert, J. Mol. Catal., 1992, 76: 123–132; A. W. Stumpf, E. Saive, A. Demonceau, and A. F. Noels, J. Chem. Soc., Chem. Commun., 1995, pages 1127–1128) reported a catalyst system which was able to effect ROMP of cyclooctenes. This catalyst system consists of (1) an $[RuCl_2(arene)]_2$ complex combined with a phosphine (tricyclohexyl- or triisopropyl-phosphine) and (2) an organic diazo compound such as trimethylsilyldiazomethane or ethyl diazoacetate. Also, recently, Grubbs et al. (P. Schwab et al., Angew. Chem. Int. Ed. Engl., 1995, 34: 2039–2041; P. Schwab, R. H. Grubbs, and J. W. Ziller, J. Am. Chem. Soc., 1996, 118: 100–110) reported a one-component ruthenium complex able to catalyze metathesis of acyclic olefins and low-strain cyclic olefins. The Grubbs catalyst was prepared by reaction of a ruthenium compound, $RuCl_2(PPh_3)_3$, with (1) an organic diazo compound such as phenyldiazomethane and (2) a bulky phosphine such as tricyclohexyl-, triisopropyl-, or tricyclopentyl-phosphine.

A disadvantage of the catalysts reported by Noels et al. and by Grubbs et al. is that an organic diazo compound is employed, either as a catalyst component (Noels et al.) or as a reagent to synthesize the catalyst (Grubbs et al.). The organic diazo compounds employed by Noels et al. and Grubbs et al. are expensive and are not commercially available in large quantities. Furthermore, many of these diazo compounds (such as phenyldiazomethane) are dangerously unstable and may explode even at room temperature (X. Creary, Org. Synth., Coll. Vol. 7, 1990, pages 438–443). The present invention, a ruthenium-based catalyst for metathesis of low-strain cyclic olefins and acyclic olefins which does not employ a diazo compound as a catalyst component or precursor, is a solution to this problem.

SUMMARY OF THE INVENTION

A ruthenium-based metathesis catalyst system which contains a ruthenium compound (A), a phosphorus compound (B), and a compound (C) containing a carbon-to-carbon triple bond. The mole ratio of compounds A:B:C is typically in the range of about 1.0:0.01–100:0.01–100. The ruthenium compound (A) is a Ru(II), Ru(III), or Ru(IV) compound containing an anionic ligand (X) and optionally an arene ligand and optionally a phosphorus compound ligand. The phosphorus compound (B) is optional if the ruthenium compound (A) contains a phosphorus-containing ligand.

A process for olefin metathesis in the presence of a catalyst system for ring-opening metathesis polymerization of cyclic olefins, metathesis of acyclic olefins, acyclic diene metathesis polymerization, cross-metathesis of cyclic and acyclic olefins, ring-closing metathesis, metathesis depolymerization of unsaturated polymers and metathesis of functionalized olefins involves reacting at least one olefin with the catalyst system described herein.

DETAILED DESCRIPTION OF THE INVENTION

The present invention provides a simple ruthenium-based catalyst for metathesis of highly strained, less-strained and low-strain cyclic olefins and acyclic olefins, and does not employ an expensive or potentially dangerous diazo compound as a catalyst component or precursor. This invention relates to a ruthenium-based catalyst system used in olefin metathesis reactions such as metathesis polymerization of cyclic olefins, olefin metathesis of acyclic olefins, metathesis of functionalized olefins, ring-opening metathesis polymerization of cyclic olefins, acyclic diene metathesis polymerization, cross-metathesis of cyclic and acyclic olefins, ring-closing metathesis, and/or metathesis depolymerization of unsaturated polymers, and to the olefin metathesis process obtained thereby. The catalyst system comprises a ruthenium compound (A), a phosphorus compound (B), and a compound (C) containing a carbon-to-carbon triple bond, where phosphorus compound (B) is optional if the ruthenium compound (A) contains a phosphorus-containing ligand.

The ruthenium compounds (A) useful in this invention include, for example, Ru(II), Ru(III), and Ru(IV) compounds containing an anionic ligand (X) and optionally containing an arene ligand and optionally a phosphorus compound ligand (e.g., phosphine or phosphite). Generally, the ruthenium compound is represented by the formula

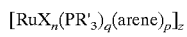

where n=2, 3, or 4; q=0, 1, 2, 3, or 4; p=0 or 1; and z=1 or 2.

X is an anionic ligand (a negatively charged moiety). X may be an aliphatic anionic ligand containing up to about 20 carbon atoms or an aromatic anionic ligand containing up to about 20 carbon atoms. X also may be selected from negatively charged groups such as halogens, hydroxides, or alkoxides, or X may be nitrate ($NO_3$), nitrite ($NO_2$), acetate ($CH_3CO_2$), trifluoroacetate ($CF_3CO_2$), acetylacetonate ($CH_3COCHCOCH_3$), hexafluoroacetylacetonate ($CF_3COCHCOCF_3$), and mixtures thereof.

The phosphorus compound ligand ($PR'_3$) may be a phosphine or phosphite. R' is selected from R and (OR) where each of the R groups of phosphite or phosphine are the same or are independent and may be selected from the group consisting of hydrogen, alkyl, cycloalkyl, aryl and arylalkyl groups, unsubstituted or substituted, each group of up to about 20 carbon atoms; the substituents may be halogen, or alkyl or aryl moieties of up to 20 carbon atoms. If R' is OR then R' and R are not hydrogen. If R' is R then at least one R is not hydrogen.

The arene ligand may be an aromatic ligand of up to about 30 carbon atoms, substituted or unsubstituted; the substituents of the substituted aromatic ligand may be selected from the group consisting of halogen, alkyl and aryl groups of up to about 25 carbon atoms, trialkylsilyl and triarylsilyl groups of up to about 25 carbon atoms, and mixtures thereof. The aromatic ligand may be selected from alkylbenzenes, polyalkylbenzenes, arylbenzenes, polyarylbenzenes, halobenzenes, haloalkylbenzenes, haloarylbenzenes, alkylnaphthalenes, arylnaphthalenes, polyalkylnaphthalenes, polyarylnaphthalenes, halonaphthalenes, haloalkylnaphthalenes, and haloarylnaphthalenes. The aromatic ligand may be, among others, benzene, toluene, xylene, cumene, cymene, p-cymene, durene, trimethylsilylbenzene, 1,4-bis(trimethylsilyl)benzene, or naphthalene.

The ruthenium compound (A) useful in the invention includes, among others, $[RuX_2(arene)]_2$, $RuX_2(arene)(PRR^1R^2)$, $RuX_2(arene)(PHRR^1)$, $RuX_2(arene)(PH_2R)$, $RuX_2(arene)[P(OR)(OR^1)(OR^2)]$, $RuX_3$, $RuX_3$-hydrate, $RuX_2(PRR^1R^2)_3$, $RuX_2(PHRR^1)_3$, $RuX_2(PH_2R)_3$, $RuX_2[P(OR)(OR^1)(OR^2)]_3$, $RuX_2(PRR^1R^2)_4$, $RuX_2(PHRR^1)_4$, $RuX_2(PH_2R)_4$, or $RuX_2[P(OR)(OR^1)(OR^2)]_4$ where P is phosphorus.

The R groups of the phosphorus compound ligand of the ruthenium compound (A), e.g, R, $R^1$ and $R^2$ above, may be the same or are independently selected from the group consisting of alkyl, cycloalkyl, aryl, and alkylaryl groups, unsubstituted or substituted, each group of up to about 20 carbon atoms (preferably up to about 12 carbon atoms, more preferably up to about 8 carbon atoms, most preferably up to about 6 carbon atoms); the substituents may be halogen (F, Cl, Br, and I), alkyl or aryl moieties of up to about 20 carbon atoms (preferably up to about 12 carbon atoms, more preferably up to about 8 carbon atoms, most preferable up to about 6 carbon atoms).

X is selected from the group consisting of an aliphatic anionic ligand (negatively charged aliphatic moiety; for example up to about 20 carbon atoms, preferably up to about 12 carbon atoms, more preferably up to about 8 carbon atoms, most preferably up to about 6 carbon atoms such as methyl, ethyl, propyl, isopropyl, butyl, hexyl), an aromatic anionic ligand (negatively charged aromatic moiety; for example of up to 20 carbon atoms, preferably up to 12 carbon atoms, more preferably up to about 8 carbon such as phenyl, benzyl). X may be selected from negatively charged groups such as halogens (F, Cl, Br, and I), hydroxides (OH), or alkoxides ($OR^3$, where $R^3$ is selected from the group consisting of alkyl, cycloalkyl, aryl, and alkylaryl groups, each group of up to about 20 carbon atoms (preferably up to about 12 carbon atoms, more preferably up to about 8 carbon atoms, most preferably up to about 6 carbon atoms)). X may be selected from nitrate ($NO_3$), nitrite ($NO_2$), acetate ($CH_3CO_2$), trifluoroacetate ($CF_3CO_2$), acetylacetonate ($CH_3COCHCOCH_3$), hexafluoroacetylacetonate ($CF_3COCHCOCF_3$), and mixtures thereof.

The arene group of said ruthenium compound (A), e.g., $[RuX_2(arene)]_2$, $RuX_2(arene)(PRR^1R^2)$, $RuX_2(arene)(PH_2R)$, $RuX_2(arene)(PHRR^1)$, and $RuX_2(arene)[P(OR)(OR^1)(OR^2)]$, is typically based on arene derivatives of benzene and naphthalene. The arene group includes an aromatic ligand of up to about 30 carbon atoms (preferably up to about 20 carbon atoms, more preferably up to about 15 carbon atoms), substituted or unsubstituted, and mixtures thereof. The number of substituents the aromatic ligand can have depends on the aromatic nucleus; for example, a benzene nucleus can have up to six substituents, a naphthalene nucleus can have up to 8 substituents. The substituents of the substituted aromatic ligand are selected from the group consisting of halogen (e.g., F, Cl, Br, I; preferably Cl), alkyl and aryl groups of up to about 25 carbon atoms (preferably up to about 20 carbon atoms, more preferably up to about 12 carbon atoms, most preferably up to about 8 carbon atoms), trialkylsilyl and triarylsilyl groups of up to about 25 carbon atoms (preferably up to about 20 carbon atoms, more preferably up to about 15 carbon atoms, most preferably up to about 8 carbon atoms), and mixtures thereof. The aromatic ligand may be selected from alkylbenzenes, polyalkylbenzenes, arylbenzenes, polyarylbenzenes, halobenzenes, haloalkylbenzenes, haloarylbenzenes, alkylnaphthalenes, arylnaphthalenes, polyalkylnaphthalenes, polyarylnaphthalenes, halonaphthalenes, haloalkylnaphthalenes, and haloarylnaphthalenes. The aromatic ligand may be, among others, benzene, toluene, xylene, cumene, cymene, p-cymene, durene, trimethylsilylbenzene, 1,4-bis(trimethylsilyl)benzene, or naphthalene.

The phosphorus compound (B) typically is selected from the group consisting of phosphine and phosphite compounds of the formulae $PR_3$, $P(OR)_3$, $PH_2R$, $PHRR^1$, $PRR^1R^2$ and $P(OR)(OR^1)(OR^2)$. R, $R^1$ and $R^2$ are the same or are independently selected from the group consisting of alkyl, cycloalkyl, aryl and arylalkyl groups, unsubstituted or substituted, each group of up to about 20 carbon atoms (preferably up to about 12 carbon atoms, more preferably up to about 8 carbon atoms, most preferably up to about 6 carbon atoms); the substituents may be halogen (F, Cl, Br, and I), alkyl or aryl moieties of up to 20 carbon atoms (preferably up to about 12 carbon atoms, more preferably up to about 8 carbon atoms, most preferably up to about 6 carbon atoms). The phosphorus compound (B) is preferably a phosphine compound, more preferably a $C_3$ to $C_8$ tri-alkyl or -cycloalkyl phosphine typically selected from the group consisting of tricyclohexylphosphine, triisopropylphosphine and tricyclopentylphosphine. The phosphorus compound (B) is optional if the ruthenium compound (A) possesses a phosphorus-containing ligand. Such ruthenium compounds (A) possessing a phosphorus-containing ligand include $RuX_2(arene)(PRR^1R^2)$, $RuX_2(arene)(PHRR^1)$, $RuX_2(arene)(PH_2R)$, $RuX_2(arene)[P(OR)(OR^1)(OR^2)]$, $RuX_2(PRR^1R^2)_3$, $RuX_2(PHRR^1)_3$, $RuX_2(PH_2R)_3$, $RuX_2[P(OR)(OR^1)(OR^2)]_3$, $RuX_2(PRR^1R^2)_4$, $RuX_2(PHRR^1)_4$, $RuX_2(PH_2R)_4$, or $RuX_2[P(OR)(OR^1)(OR^2)]_4$ where P is phosphorus; these compounds are described in detail above.

Catalyst compound (C), the compound containing a carbon-to-carbon triple bond, can be a substituted or unsubstituted $C_2$ to $C_{20}$ alkyne (preferably up to about 16 carbon atoms, more preferably up to about 12 carbon atoms, most preferably up to about 8 carbon atoms) such as a terminal alkyne, an internal alkyne, or an alkyne possessing one or more (e.g., 1 or 2) aliphatic or aromatic functional substituent groups (preferably up to about 20 carbon atoms, more preferably up to about 12 carbon atoms, most preferably up to about 8 carbon atoms), halogen (F, Cl, Br, and I), ester, hydroxyl, ketone, aldehyde, ether, carboxyl, amide, anhydride, nitrile, silyl or amine functional substituent groups, and mixtures thereof. Catalyst compound (C) can be selected from the group consisting of acetylene ($C_2H_2$), propyne, 1-butyne, 2-butyne, 1-pentyne, 2-pentyne, 1-hexyne, 2-hexyne, 3-hexyne, 1-heptyne, 1-octyne, 1-decyne, 1-dodecyne, trimethylsilylacetylene, phenylacetylene, diphenylacetylene, 2-butyne-1,4-diol, ester derivatives of 2-butyne-1,4-diol such as 1,4-diacetoxy-2-butyne, 2-butyne-1,4-diol monoacetate, 2-butyne-1,4-diol diacetate, 2-butyne-1,4-diol monopropionate, 2-butyne-1,4-diol dipropionate, 2-butyne-1,4-diol monobenzoate, and 2-butyne-1,4-diol dibenzoate.

Mole ratios of A:B:C, expressed as compounds, are typically in the range of 1:0.01–100:0.01–100 (preferably 1.0:0.1–40:0.1–40, more preferably 1.0:0.2–20:0.2–20). Mole ratios of A:B, expressed as compounds, are typically in the range of 1:0.01–100 (preferably 1.0:0.1–40, more preferably 1.0:0.2–20).

It has been found that the presence of hydrogen ($H_2$) improves catalytic activity, reactant conversion, and product yield. The presence of hydrogen (typically at a partial pressure of hydrogen of from about $1\times10^{-2}$ mm Hg to about 200 atmospheres, preferably from about 0.1 mm Hg to about 100 atmospheres, more preferably 1 mm Hg to about 20 atmospheres, though generally pressure is not critical) as a catalyst system activator improves the catalyst activity, reactant conversion, and product yield in the process of the invention.

The catalyst system is employed in processes to metathesize olefins, including ring-opening metathesis polymerization of cyclic olefins, metathesis of acyclic olefins, acyclic diene metathesis oligomerization or polymerization, cross-metathesis of cyclic and acyclic olefins, ring-closing metathesis, metathesis depolymerization of unsaturated polymers, and metathesis of functionalized olefins. The catalyst system can successfully metathesize highly-strained cyclic olefins (e.g., norbornene and norbornene derivatives, norbornadiene, cyclobutene and cyclobutene derivatives, and dicyclopentadiene) as well as less-strained cyclic olefins (e.g., cyclopentene, cycloheptene, cyclooctene, or 1,5-cyclooctadiene, cyclodecene, cyclododecene, and 1,5,9-cyclododecatriene). Olefins containing functional groups such as ester, hydroxyl, ketone, aldehyde, ether, carboxyl, amide, anhydride, nitrile, halogen (F, Cl, Br, and I), and/or amine moieties can also be metathesized.

It is preferable that an activator be present as a component of the catalyst system for increased catalytic activity, increased reactant conversion and increased product yield. It has been found that hydrogen, $H_2$, acts as an activator of the catalyst system. It is assumed that the solubility of hydrogen in the liquid phase (with the liquid phase consisting of the reactant olefins either in neat form or dissolved in a solvent) aids in the catalytic activity of the catalyst system. It is well-known that hydrogen is soluble in solvents with greater solubility of hydrogen in liquid media with increased pressure (A. Seidell, *Solubilities of Inorganic and Metal Organic Compounds*, Vol. 1, D. Van Nostrand Co., N.Y., N.Y., 1940, p. 564–567). Such solvents include the solvents listed below.

The catalyst system alternatively can comprise a catalyst component to dehydrogenate a hydrogen-containing compound as an in-situ source of hydrogen under the reaction conditions of the process, such as the dehydrogenation of tetralin to naphthalene and $H_2$, and dehydrogenation of cyclohexyl alcohol to $H_2$ and cyclohexanone in the presence of ruthenium on activated carbon; such dehydrogenation reactions are well known in the art.

The catalyst system employed is dissolved or suspended in a liquid phase, with the liquid phase consisting primarily of the reactant olefins either in neat form or dissolved in a solvent. A variety of solvents may be employed, including aliphatic solvents such as pentane, hexane, heptane, decane, decalin, and dichloromethane, aromatics such as benzene, toluene, xylenes, chlorobenzene, and dichlorobenzene, and others such as diethyl ether and tetrahydrofuran. The catalyst system can be employed under an atmosphere of nitrogen, argon, helium, air, carbon dioxide, or hydrogen, and typically at a pressure from below atmospheric (i.e., under vacuum) up to about 200 atmospheres. A hydrogen atmosphere is preferred. Generally, a wide range of temperatures, pressures and reaction times can be used. The olefin metathesis process employing the invented catalyst system can typically be at a temperature of from about 0° C. to about 250° C. (preferably about 0° C. to about 200° C., more preferably about 0° C. to about 150° C.), and typically at a pressure of from about $1\times10^{-2}$ mm Hg to about 200 atmospheres (preferably about 0.1 mm Hg to about 100 atmospheres, more preferably about 1 mm Hg to about 20 atmospheres). Typically, the reaction time (or residence time in a continuous reaction) for the olefin metathesis process employing the invented catalyst system can be from about one second to about one day; preferably from about five minutes to about 10 hours.

It has been found that linear functional acyclic olefinic compounds comprising monofunctional unsaturated polymers containing functional groups can be prepared in the presence of the catalyst composition of this invention in cross-metathesis reactions with acyclic or cyclic olefinic non-conjugated compounds.

In the presence of reactants comprising cyclic olefinic non-conjugated compounds and polymeric olefinic compounds with functional olefinic compounds, linear difunctional telechelic unsaturated polymers are prepared with at least one internal carbon-to-carbon double bond and terminal groups. These linear non-crosslinked difunctional telechelic unsaturated polymers with reactive terminal groups are suitable for further functionalization or incorporation into other polymers for preparation of block copolymers and other products.

The linear non-crosslinked difunctional telechelic unsaturated polymers prepared by the process of this invention are typically true linear compounds of strictly regular structure with exactly defined terminal groups.

As is well known, side reactions may occur during olefin metathesis reactions. These side reactions include alkylation, isomerization, cyclization and addition across double bonds present in the molecular structure. Surprisingly, it has been found that these side reactions are minimal in cross-metathesis reactions under the conditions of the present invention. The average functionality number of monofunctional polymers prepared by the process of this invention is at least 0.7 (e.g., 0.7 to 1.0) as determined by nuclear magnetic resonance spectroscopy ($^{13}$C NMR which is well known in the art). The average functionality number of telechelic difunctional polymers prepared by the process of this invention is at least 1.7 (e.g., 1.7 to 2.0), as determined by nuclear magnetic resonance spectroscopy ($^{13}$C NMR). The functionality number is determined by the nuclear magnetic resonance spectroscopy procedure described by Nubel, P. O., et al., "Preparation of an ester-terminated telechelic polybutadiene by a two-step olefin metathesis process", *Journal of Molecular Catalysis A: Chemical* (1997), 115: 43–50.

The monofunctional polymers and telechelic difunctional polymers prepared by the process of the instant invention are prepared by metathesis reactions which are cross-metathesis reactions between acyclic olefinic compounds or cross-metathesis reactions between cyclic and acyclic olefinic compounds. Cross-metathesis reactions have been generally classified as being of three categories: (1) exchange of atoms between two olefinic compounds to produce two different olefinic compounds, (2) ring-opening of a cyclic olefinic compound to produce acyclic polymers, and (3) degradation of olefinic polymers to produce oligomers of lower molecular weight. The reactions of the present invention are of the three categories.

Non-crosslinked linear monofunctional and telechelic difunctional polymers obtained by the process of this invention are defined as polymers consisting essentially of strictly linear hydrocarbon chains comprising repeating monomer units of 3 to 30 carbon atoms, said hydrocarbon chains without any side chains or pendant groups which would cause cross-linking. The number of monomer repeating units can be from 3 to about 10,000.

Non-crosslinked linear monofunctional telechelic polymers prepared by the process of this invention are defined as monofunctional polymers having a terminal functional reactive group and an average functionality number which is at least 0.7, as determined by NMR. Non-crosslinked linear difunctional telechelic polymers prepared by the process of this invention are defined as difunctional polymers containing terminal functional end-groups and the average functionality number is at least 1.7, as determined by NMR.

The present invention provides a metathesis catalytic process for preparing non-crosslinked monofunctional and telechelic difunctional polymers from monofunctional olefinic compounds wherein the functionality of a monofunctional polymer is at least 0.7 and the average functionality of a difunctional polymer is at least 1.7, as determined by NMR (nuclear magnetic resonance). The present invention also provides monofunctional and difunctional unsaturated polymers wherein the functional groups are reactive terminal groups and thus are positioned for further functionalization and/or incorporation into other reactive compounds. The present invention also may be used to prepare monofunctional and telechelic difunctional polymers wherein the functional component comprises a terminal functional group, particularly an ester group such as an acetoxy group. Functional groups are defined herein as including ester, hydroxyl, ketone, aldehyde, ether, carboxyl, amide, anhydride, nitrile, halogen (F, Cl, Br, and I), and/or amine moieties.

The following examples are exemplary only and are not to be considered as limiting the scope of the invention:

Examples 1–5 demonstrate the ability of this catalyst system to effect ring-opening olefin metathesis polymerization of a low-strain cyclic olefin, cis,cis-1,5-cyclooctadiene ("1,5-COD"), as well as the olefin metathesis of an acyclic olefin containing ester functional groups, cis-1,4-diacetoxy-2-butene ("cis-1,4-DAB"). The catalyst system was employed to carry out the cross-metathesis of 1,5-COD with 1,4-DAB to yield acetate-terminated 1,4-polybutadiene:

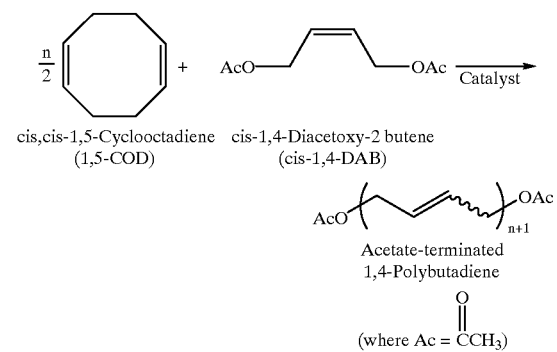

EXAMPLE 1

This example illustrates the effect of the presence of a compound containing a carbon-to-carbon triple bond wherein the mole ratio of ruthenium compound (A) to phosphorus compound (B) and carbon-to-carbon triple bond (C) is 1.0:4.0:0.22. Conversion of 1,5-cyclooctadiene (1,5-COD), in the presence of 1,4-diacetoxy-2-butene, 1,4-DAB, to acetate-terminated 1,4-polybutadiene in an inert atmosphere of nitrogen after a reaction time of 3 hours at 90° C. was 35 wt. % with a corresponding conversion of 1,4-DAB to 17 wt. %. After 22 hours at 90° C., conversion to acetate-terminated 1,4-polybutadiene of the 1,4-COD was 39 wt. % and 1,4-DAB was 27 wt. %.

A solution consisting of 0.098 g [(RuCl$_2$(p-cymene)]$_2$ (0.16 mmol, Strem Chemicals, Inc.,) 0.18 g tricyclohexylphosphine (0.64 mmol, Aldrich), 3.7 mL cis-1,4-diacetoxy-2-butene ("cis-1,4-DAB", 23 mmol, 95+ % purity, TCI America, lot number FCZ02), 15.0 mL cis,cis-1,5-cyclooctadiene ("1,5-COD", 122 mmol, 99.9% purity by GC analysis), and 35 mL chlorobenzene (Aldrich HPLC grade, dried over 4A molecular sieves) was charged into a 100-mL glass round-bottom flask under N$_2$ at atmospheric pressure (15 psia). Flame ionization detector (FID) gas chromatographic (GC) analysis of the cis-1,4-DAB indicated that it contained 0.15 wt. % of the alkyne 1,4-diacetoxy-2-butyne; thus, the above solution contained 0.035 mmol 1,4- diacetoxy-2-butyne (thus the commercial cis-1,4-DAB product contained 1,4-diacetoxy-2-butyne). The flask containing the solution was immersed in a 90° C. oil bath and the solution was magnetically stirred under nitrogen atmosphere. After 3 hours at 90° C. FID GC analysis of the solution indicated that COD conversion was 35 wt. % and DAB conversion was 17 wt. %. After 22 hours (at 90° C.) GC analysis indicated that COD conversion was 39 wt. % and DAB conversion was 27 wt. %. The reaction solution was then cooled to room temperature. Chlorobenzene solvent, COD, and some of the remaining DAB were removed by rotary evaporation under vacuum (1.5 hours at 80–95° C., 0.2–0.4 mm Hg), affording 5.2 grams of a brown, low-viscosity oily liquid product. This product contained some remaining DAB (6 wt. % as indicated by $^{13}C$ NMR analysis). GPC analysis of the product was as follows: $M_n$=370, $M_w$=2590, $M_w/M_n$=7 (tetrahydrofuran (THF) solvent; polybutadiene calibration; calculation of molecular weights included remaining DAB).

A sample of the product was dissolved in $CDCl_3$ and analyzed by $^{13}C$ and $^1H$ NMR spectroscopy using a Varian VXR-300 spectrometer. (Chromium acetylacetonate was added to the solution as a relaxation agent for $^{13}C$ NMR studies). NMR analyses indicated that the product possessed a 1,4-polybutadiene backbone structure with a 72:28 cis/trans carbon-carbon double bond ratio. The proportion of chain end groups observed by $^{13}C$ NMR was 97 mole % acetate-type endgroups (—$CH_2OC(O)CH_3$) and 3 mole % vinyl endgroups (—CH=$CH_2$).

The analyses indicate that the product was a low molecular weight polybutadiene material with acetate-type functional groups as the predominant type of chain end group. This is the expected product of the cross-metathesis reaction of 1,5-COD with 1,4-DAB. Details are in Table 1.

EXAMPLE 2

This example was performed according to the procedure of Example 1 except that the reaction was performed under an atmosphere of hydrogen ($H_2$) at atmospheric pressure (15 psia) and demonstrates the beneficial effect of hydrogen upon catalytic activity, reactant conversion, and product yield. The presence of hydrogen, $H_2$, caused the conversion of 1,5-cyclooctadiene in the presence of 1,4-diacetoxy-2-butene to acetate-terminated 1,4-polybutadiene to increase from 35 wt. %, as in Example 1, to 70 wt. %. A corresponding increase in conversion of 1,4-diacetoxy-2-butene from 17 wt. %, Example 1, to 34 wt. % also occurred.

A separate solution consisting of 0.098 g [$RuCl_2$(p-cymene)]$_2$ (0.16 mmol, Strem Chemicals, Inc.), 0.18 g tricyclohexylphosphine (0.64 mmol, Aldrich), 3.7 mL cis-1,4-diacetoxy-2-butene ("cis-1,4-DAB", 23 mmol, 95+ % purity, TCI America, lot number FCZ02), 15.0 mL cis-cis-1,5-cyclooctadiene ("1,5-COD", 122 mmol, 99.9% purity by GC analysis), and 35 mL chlorobenzene (Aldrich HPLC grade, dried over 4A molecular sieves) was charged into a 100-mL glass round-bottom flask under $N_2$ atmosphere. FID GC analysis of the cis-1,4-DAB indicated that it contained 0.15 wt. % of the alkyne 1,4-diacetoxy-2-butyne; thus, the solution contained 0.035 mmol 1,4-diacetoxy-2-butyne. The flask was immersed in a 90° C. oil bath. Hydrogen gas ($H_2$) was then bubbled through the solution in the flask at atmospheric pressure (15 psia) for 10 minutes at 100 mL/min flow rate. (The hydrogen gas passed into the solution from the immersed tip of a stainless steel syringe needle, and exited the flask through tubing connected from the headspace of the flask to an oil bubbler). After the 10 minutes, the flow of the hydrogen into the flask was ceased. The solution was then stirred magnetically at 90° C. under the static hydrogen atmosphere (15 psia). After 3 hours (at 90° C.) GC analysis of the solution indicated that COD conversion was 70 wt. % and DAB conversion was 34 wt. %. After 22 hours (at 90° C.) GC analysis indicated that COD conversion was 76 wt. % and DAB conversion was 44 wt. %. It is to be noted that these conversions are approximately twice as high as those that were obtained in Example 1. The only change from Example 1 was the presence of hydrogen.

The reaction solution was then cooled to room temperature. Chlorobenzene solvent, COD, and some of the remaining DAB were removed by rotary evaporation under vacuum (1 hour at 80° C., 0.2 mm Hg), affording 10.75 grams of a brown, low-viscosity oily liquid product. It is to be noted that this yield of crude product is about twice that obtained in Example 1. This crude product contained some remaining DAB (4 wt. % as indicated by $^{13}C$ NMR analysis). GPC analysis of the crude product was as follows: $M_n$=410, $M_w$=2200, $M_w/M_n$=5.4 (THF solvent; polybutadiene calibration; calculation of molecular weights included remaining DAB). A sample of the crude product was dissolved in chloroform-d ($CDCl_3$) and analyzed by $^{13}C$ and $^1H$ NMR spectroscopy using a Varian VXR-300 spectrometer. (Chromium acetylacetonate was added to the solution as a relaxation agent for $^{13}C$ NMR studies). NMR analyses indicated that the product possessed a 1,4-polybutadiene backbone structure with a 69:31 cis/trans carbon-carbon double bond ratio. The proportion of chain end groups observed by $^{13}C$ NMR was 98 mole % acetate-type endgroups (—$CH_2OC(O)CH_3$) and 2 mole % vinyl endgroups (—CH=$CH_2$).

The analyses indicate that this product was a low molecular weight polybutadiene material with acetate-type functional groups as the predominant type of chain end group. This is the expected product of the cross-metathesis reaction of 1,5-COD with 1,4-DAB.

This product was further treated to remove catalyst residues and DAB as follows. The product (~8.4 grams) was dissolved in chlorobenzene (25 mL) containing 50 mg butylated hydroxytoluene (BHT). This solution was filtered through a 1-inch diameter column containing 20 grams of 200-mesh silica gel (Aldrich). Afterward the column was washed with chlorobenzene (5×50 mL) and the washings were added to the filtrate. Removal of solvent by rotary evaporation under vacuum afforded 5.6 grams of a light brown oil. The oil was washed twice with 70-mL portions of methanol; the washes were performed by vigorously stirring the methanol/oil mixture at room temperature, allowing the mixture to stand for phases to separate, and then removing and discarding the methanol phase. Residual methanol was removed from the washed oil by rotary evaporation under vacuum (1 hour at 80° C., 0.4 mm Hg), affording 4.8 grams of a light brown, low-viscosity oily liquid product (labeled 19303-155). GPC analysis of this treated product was as follows: $M_n$=840, $M_w$=2490, $M_w/M_n$=3.0 (THF solvent; polybutadiene calibration). NMR analyses (as described above) indicated that the treated product contained less than 0.5 wt. % DAB. NMR analyses also indicated that the treated product possessed a 1,4-polybutadiene backbone structure with a 69:31 cis/trans carbon-carbon double bond ratio and that the proportion of chain end groups was 98 mole % acetate-type endgroups and 2 mole % vinyl endgroups. Ruthenium content was measured at 0.047 wt. % by XRF analysis. Details are in Table 1.

EXAMPLE 3

This example illustrates the effect of changing the mole ratio of catalyst components, A:B:C, to 1.0:2.0:0.44, as compared with catalyst component ratio of Examples 1 and 2. Reaction temperature was decreased to 60° C. from 90° C. Reaction time increased to 4 hours from 3 hours. Reaction pressure was increased from atmospheric pressure (15 psia), as in Examples 1 and 2, to 17 psig under $H_2$ gas. Conversion of 1,4-COD increased to 57 wt. % as compared with 1,4-COD conversion of Example 1, 35 wt. %, but decreased from 70 wt. % of Example 2.

A solution consisting of 0.098 g $[RuCl_2(p\text{-cymene})]_2$ (0.16 mmol), 0.090 g tricyclohexylphosphine (0.32 mmol), 7.4 mL cis-1,4-DAB (47 mmol), 30.0 mL 1,5-COD (244 mmol), and 10 mL chlorobenzene was charged into a 6-oz glass Fisher-Porter bottle under $N_2$ atmosphere (15 psia). Due to the presence of 0.15 wt. % 1,4-diacetoxy-2-butyne in the cis-1,4-DAB, the solution contained 0.07 mmol 1,4-diacetoxy-2-butyne. The bottle was sealed and then immersed in a 60° C.-oil bath and the solution was magnetically stirred for 20 minutes to dissolve all the solids. The bottle was then pressurized to 17 psig with hydrogen gas ($H_2$). After pressurization, the bottle was sealed off under static hydrogen pressure (valve to hydrogen source was closed) and the solution was stirred for 4 hours (since hydrogen pressurization) at 60° C. At the end of the 4 hours, the pressure in the bottle had decreased to 6 psig. The bottle was cooled to room temperature and depressurized, and the solution was analyzed by FID GC to determine reactant conversions. Calculated COD conversion was 57 wt. %; DAB conversion was 27 wt. %.

The reaction solution was decolorized by adding 5 grams charcoal (100-mesh Darco G-60 brand) and 50 mg BHT, stirring the solution at room temperature under $N_2$ for about ½ hour, and filtering off the charcoal. Chlorobenzene solvent, COD, and most of the remaining DAB were removed by rotary evaporation under vacuum (1 hour at 90° C., 0.1–1 mm Hg), affording 12.6 grams of a yellow, oily liquid crude product. The crude product was then washed three successive times with 150 mL portions of methanol; the washes were performed by vigorously stirring the methanol/oil mixture at room temperature, allowing the mixture to stand for phases to separate, and then removing and discarding the methanol phase. Residual methanol was removed from the washed oil by rotary evaporation under vacuum (90° C., 0.1–1 mm Hg), affording 9.5 grams of a yellow, oily liquid final product.

GPC analysis of the final product was as follows: $M_n=1400$, $M_w=2620$, $M_w/M_n=1.9$ (THF solvent; polybutadiene calibration). NMR analyses (as described above, except using a Varian Unity-500 spectrometer) indicated that the final product possessed a 1,4-polybutadiene backbone structure with a 69:31 cis/trans carbon-carbon double bond ratio and that the proportion of chain end groups was 99+ mole % acetate-type endgroups and less than 1 mole % vinyl endgroups. Also, the NMR analyses indicated that about 1% or less of the carbon-carbon double bonds in the polybutadiene backbone were hydrogenated (relative to a pure unsaturated 1,4-polybutadiene backbone structure). Ruthenium content was measured at 174 ppm by XRF analysis. Details are in Table 1.

EXAMPLE 4

This example illustrates the effect of increasing the mole ratio of the carbon-to-carbon triple bond (C) in catalyst components A:B:C, to 1.0:2.0:3.0, an increase in component (C) of approximately 7-fold. All other reaction conditions were as in Example 3. Conversion of 1,4-COD increased to 86 wt. % from 57 wt. % of Example 3.

This example was performed according to the procedure of Example 3 except that additional 1,4-diacetoxy-2-butyne was added to the reaction solution. To do this, a stock solution of 1,4-diacetoxy-2-butyne (0.82 g, Aldrich) in chlorobenzene (10 mL total solution volume) was prepared. A 1.0 mL portion of this stock solution, corresponding to 0.48 mmol (0.082 g), 1,4-diacetoxy-2-butyne, was added to a reaction solution consisting of 0.098 g $[RuCl_2(p\text{-cymene})]_2$ (0.16 mmol), 0.090 g tricyclohexylphosphine (0.32 mmol), 7.4 mL cis-1,4-DAB (47 mmol), 30.0 mL 1,5-COD (244 mmol), and 10 mL chlorobenzene solvent in a 6-oz. glass Fisher-Porter bottle under $N_2$ atmosphere (15 psia). The reaction was performed at 60° C. with an initial hydrogen pressure of 17–18 psig. After 4 hours reaction time the bottle pressure had decreased to 13 psig. GC analyses after 4 hours reaction time indicated 86% COD conversion and 46% DAB conversion, substantially greater than the conversions obtained in Example 3 (which did not have additional 1,4-diacetoxy-2-butyne added to the reaction solution). Also, GC analyses indicated essentially complete conversion of the 1,4-diacetoxy-2-butyne after 4 hours reaction time.

The reaction product was decolorized, washed, and isolated by the procedure described in Example 3. Crude product was obtained in 20.4 gram yield; 15.7 grams of the final product, a light-brown oily liquid, was obtained. Both yields are substantially greater than those obtained in Example 3. GPC analysis of the final product was as follows: $M_n=1150$, $M_w=2140$, $M_w/M_n=1.9$ (THF solvent; polybutadiene calibration). NMR analyses (as described in Example 3) indicated that the final product possessed a 1,4-polybutadiene backbone structure with a 63:37 cis/trans carbon-carbon double bond ratio and that the proportion of chain end groups was 99.5+ mole % acetate-type endgroups and less than 0.5 mole % vinyl endgroups. Also, the NMR analyses indicated that less than 1% of the carbon-carbon double bonds in the polybutadiene backbone were hydrogenated (relative to a pure unsaturated 1,4-polybutadiene backbone structure). Ruthenium content was measured at 86 ppm by XRF analysis. Details are in Table 1.

The acetate-terminated polybutadiene products of Examples 3 and 4 can be converted to hydroxyl-terminated polybutadiene products by thermal or catalyzed hydrolysis or alcoholysis reactions, such as base- or acid-catalyzed hydrolysis:

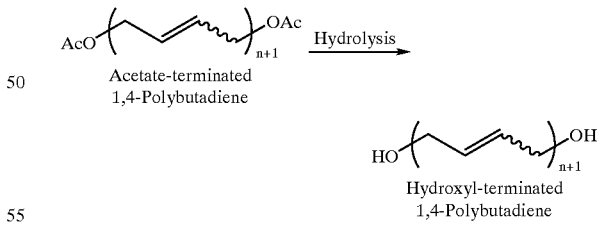

Acetate-terminated
1,4-Polybutadiene

Hydroxyl-terminated
1,4-Polybutadiene

EXAMPLE 5

This example demonstrates the beneficial effect that the hydrogen catalyst activator has with respect to increasing reaction rate and reactant conversions in the olefin metathesis reaction.

This example was performed according to the procedure of Example 4 except that the reaction was performed without the presence of hydrogen; the reaction of this example was performed under $N_2$ atmosphere (15 psia). (The only other difference was that 9 mL chlorobenzene solvent was employed instead of 10 mL as in Example 4). After 4 hours reaction time (at 60° C.), GC analyses indicated only 5% COD conversion and no detectable DAB conversion. Details are in Table 1.

Examples 6–9 demonstrate the ability of this catalyst system to effect the ring-opening metathesis polymerization (ROMP) of a low-strain cyclic olefin, cis,cis-1,5-cyclooctadiene ("1,5-COD"), to yield 1,4-polybutadiene:

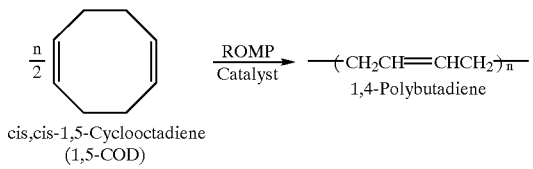

cis,cis-1,5-Cyclooctadiene
(1,5-COD)

1,4-Polybutadiene

EXAMPLE 6

This example illustrates ring-opening metathesis polymerization of a cyclic olefin to prepare a high molecular weight polymer in the presence of a catalyst comprising a ruthenium compound (A), a phosphorus compound (B), and a carbon-to-carbon triple bond (C), wherein the mole ratio of A:B:C is 1.0:2.0:3.0.

The alkyne employed was a non-terminal alkyne, 3-hexyne. A stock solution of 3-hexyne (Aldrich) in chlorobenzene was prepared with a concentration of 0.039 g 3-hexyne/mL. A reaction solution consisting of 0.098 g [RuCl$_2$(p-cymene)]$_2$ (0.16 mmol), 0.090 g tricyclohexylphosphine (0.32 mmol), 1.0 mL of the 3-hexyne stock solution (0.48 mmol 3-hexyne), 30.0 mL 1,5-COD (244 mmol), and 9 mL chlorobenzene solvent was charged into a 6-oz. glass Fisher-Porter bottle under N$_2$ atmosphere (15 psia). The bottle was sealed and then immersed in a 60° C.-oil bath and the solution was magnetically stirred for several minutes to dissolve all the solids. The bottle was then pressurized to 20 psig with hydrogen gas (H$_2$). After pressurization, the bottle was sealed off under static hydrogen pressure (valve to hydrogen source was closed) and the solution was stirred for 4 hours (since hydrogen pressurization) at 60° C. At the end of the 4 hours the bottle pressure had decreased to 2 psig and the reaction solution was much more viscous and difficult to stir than at the start of the reaction. The bottle was cooled to room temperature and depressurized, and the solution was analyzed by FID GC. Calculated COD conversion was 8.5 wt. %.

The reaction solution was diluted with heptane. BHT (50 mg) and charcoal (5.5 g, 100-mesh Darco G-60 brand) were added. The solution was stirred at room temperature and the charcoal was then removed by filtration. Solvents and volatiles were removed from the filtrate by rotary evaporation under vacuum (95° C., 0.1–1 mm Hg), affording 1.4 grams of a dark greenish, tacky, gummy solid product. GPC analysis of the product was as follows: M$_n$=134,000, M$_w$=280,000, M$_w$/M$_n$=2.1 (THF solvent; polystyrene calibration). $^{13}$C and $^1$H NMR analyses (as described in Example 3) indicated that the product possessed a non-hydrogenated 1,4-polybutadiene backbone structure with a 75:25 cis/trans carbon-carbon double bond ratio. The analyses indicate that the product was high molecular weight 1,4-polybutadiene, the expected product of ring-opening metathesis polymerization (ROMP) of 1,5-cyclooctadiene. Details are in Table 1.

EXAMPLE 7

This example illustrates the effect of component (C), the carbon-to-carbon triple bond component of the catalyst system, wherein the alkyne is a terminal alkyne. Conversion of the 1,4-COD increased to 56 wt. % from 8.5 wt. % of Example 6, wherein the alkyne was a non-terminal alkyne.

The alkyne employed was a terminal alkyne, 1-decyne. This example was performed by the procedure of Example 6 except that 1-decyne (0.48 mmol, Aldrich) was employed in place of 3-hexyne in the reaction solution. A stock solution of 1-decyne in chlorobenzene was prepared with a concentration of 0.066 g 1-decyne/mL, and 1.0 mL of this stock solution was employed in the reaction solution. The bottle containing the reaction solution was pressurized to 15 psig with hydrogen. After 45 minutes at 60° C. the viscosity of the solution had increased so greatly that the magnetic stirring had ceased. After 4 hours reaction time at 60° C. the solution was nearly solid in texture and consistency, and the bottle pressure had decreased to 12 psig. The bottle was then cooled to room temperature and depressurized. GC-calculated COD conversion was 56 wt. %.

Solvents and volatiles were removed from the reaction solution by rotary evaporation under vacuum, affording 11.5 grams of a dark-colored, tacky solid product. GPC analysis of the product was as follows: M$_n$=112,000, M$_w$=280,000, M$_w$/M$_n$=2.5 (THF solvent; polystyrene calibration). $^{13}$C and $^1$H NMR analyses (as described in Example 3) indicated that the product possessed a non-hydrogenated 1,4-polybutadiene backbone structure with a 68:32 cis/trans carbon-carbon double bond ratio. The analyses indicate that the product was high molecular weight 1,4-polybutadiene, the expected product of ring-opening metathesis polymerization (ROMP) of 1,5-cyclooctadiene. Details are in Table 1.

EXAMPLE 8

This example illustrates effect of a substituted non-terminal alkyne as component (C) of the catalyst system, wherein the alkyne is 1,4-diacetoxy-2-butyne. Conversion of the 1,4-COD decreased to 43 wt. % from the 56 wt. % conversion of Example 7.

The alkyne employed was 1,4-diacetoxy-2-butyne. This example was performed by the procedure of Example 6 except that 1,4-diacetoxy-2-butyne (0.48 mmol, Aldrich) was employed in place of 3-hexyne in the reaction solution. A stock solution of 1,4-diacetoxy-2-butyne in chlorobenzene was prepared with a concentration of 0.082 g 1,4-diacetoxy-2-butyne/mL, and 1.0 mL of this stock solution was employed in the reaction solution. The bottle containing the reaction solution was pressurized to 16 psig with hydrogen. After 30 minutes at 60° C. the viscosity of the solution had increased so greatly that the magnetic stirring had ceased. After 3 hours reaction time at 60° C., the solution was rubbery solid in texture and consistency, and the bottle pressure had decreased to 14–15 psig. The bottle was then cooled to room temperature and depressurized. GC-calculated COD conversion was 43%. The polymer product was not isolated. Details are in Table 1.

EXAMPLE 9

No alkyne was employed. This example demonstrates the need for the alkyne (a component containing a carbon-to-carbon triple bond) catalyst component in order for the catalyst system to effectively catalyze the olefin metathesis reaction.

This example was performed by the procedure of Example 8 except that no alkyne (1,4-diacetoxy-2-butyne) was employed. After 4 hours reaction time at 60° C. the bottle pressure had decreased to 2 psig and no increase in reaction solution viscosity was observed. The bottle was then cooled to room temperature and depressurized. GC-calculated COD conversion was 0%. Details are in Table 1.

TABLE 1

| Exam-ple | Catalyst Components (mmol) | | | Reactants (mmol) | | Reaction Conditions | | Conversion (wt. %) | |
|---|---|---|---|---|---|---|---|---|---|
| | A | B | C | 1,4-DAB | 1,5-COD | °C. | Hrs. | COD | DAB |
| 1 | 0.16 | 0.64 | 0.035 | 23 | 122 | 90 | 3 | 35 | 17 |
| 2 | 0.16 | 0.64 | 0.035 | 23 | 122 | 90 | 3 | 70 | 34 |
| 3 | 0.16 | 0.32 | 0.07 | 47 | 244 | 60 | 4 | 57 | 27 |
| 4 | 0.16 | 0.32 | 0.48 | 47 | 244 | 60 | 4 | 86 | 46 |
| 5 | 0.16 | 0.32 | 0.48 | 47 | 244 | 60 | 4 | 5 | 0 |
| 6 | 0.16 | 0.32 | 0.48 | 0 | 244 | 60 | 4 | 8.5 | — |
| 7 | 0.16 | 0.32 | 0.48 | 0 | 244 | 60 | 4 | 56 | — |
| 8 | 0.16 | 0.32 | 0.48 | 0 | 244 | 60 | 3 | 43 | — |
| 9 | 0.16 | 0.32 | 0 | 0 | 244 | 60 | 4 | 0 | — |

Notes:
Catalyst components in mmol, expressed as compounds
A = Ruthenium constituent
B = Phosphorus constituent
C = Carbon-to-carbon triple bond constituent

EXAMPLES 10–13

Examples 10–13 were performed according to the procedure of Example 1 except that amount of catalyst component (B), the phosphorus compound, expressed as moles of compound was increased step-wise to illustrate the effect of an increased presence of a phosphorus compound as a component of the catalyst system. All other reaction conditions were as of the procedure which follows.

A solution consisting of 0.049 g [(RuCl$_2$(p-cymene)]$_2$ (0.080 mmol, Strem Chemicals, Inc.), 0.022–0.090 g tricyclohexylphosphine (0.080–0.32 mmol), 0.082 g 1,4-diacetoxy-2-butyne (0.48 mmol, Narchem Corp., 98% purity), 7.4 mL cis-1,4-DAB (47 mmol), 30.0 mL 1,5-COD (244 mmol, 99.9% purity by GC analysis), and 10 mL chlorobenzene solvent was prepared in a 6-oz glass Fisher-Porter bottle under nitrogen atmospheric pressure (15 psia). The bottle was sealed and then immersed in a 60° C. oil bath. The solution was magnetically stirred until the solids were dissolved. The bottle was then pressurized to 15–20 psig with hydrogen gas (H$_2$). After pressurization, the bottle was sealed off under static hydrogen pressure (valve to hydrogen source was closed). The solution was stirred for 4 hours after hydrogen pressurization at 60° C. The bottle was then cooled to room temperature and depressurized. The solution was analyzed by FID GC to determine reactant conversion. Details for Examples 10–13 are in Table 2.

TABLE 2

| Example | Catalyst Components | | | | | | Reaction Conditions | | Conversion (wt. %) | |
|---|---|---|---|---|---|---|---|---|---|---|
| | A | | B | | C | | H$_2$ (psig) | °C. | DAB | COD |
| | g | mmol | g | mmol | g | mmol | | | | |
| 10 | 0.049 | 0.080 | 0.022 | 0.080 | 0.082 | 0.48 | 20 | 60 | 3 | 9 |
| 11 | 0.049 | 0.080 | 0.045 | 0.16 | 0.082 | 0.48 | 15 | 60 | 31 | 71 |
| 12 | 0.049 | 0.080 | 0.067 | 0.24 | 0.082 | 0.48 | 18–16 | 60 | 36 | 76 |
| 13 | 0.049 | 0.080 | 0.090 | 0.32 | 0.082 | 0.48 | 18–16 | 60 | 16 | 46 |

Notes:
A = [RuCl$_2$(p-cymene)]$_2$
B = Tricyclohexylphosphine
C = 1,4-diacetoxy-2-butyne

EXAMPLES 14–15

Examples 14 and 15 were performed to demonstrate the effect of increased hydrogen gas (H$_2$) pressure.

A solution was prepared consisting of [RuCl$_2$(p-cymene)]$_2$, tricyclohexylphosphine, 1,4-diacetoxy-2-butyne, and reactants cis-1,4-diacetoxy-2 -butene (cis-1,4-DAB) (7.4 mL, 47 mmol) and cis,cis-1,5-cyclooctadiene (1,5-COD) (30.0 mL, 244 mmol), and 10 mL chlorobenzene solvent in a 6-oz glass Fisher-Porter bottle under nitrogen at atmospheric pressure (15 psia). The bottle was sealed and immersed in a 60° C. oil bath. The solution was magnetically stirred to dissolve all the solids. The bottle was then pressurized to desired initial pressure with hydrogen gas (H$_2$). After pressurization, the bottle was sealed off under static hydrogen pressure, the valve to hydrogen source was closed, and the solution was stirred for 4 hours, since hydrogen pressurization, at 60°. The bottle was cooled to room temperature, then depressurized. The solution was analyzed by FID GC to determine reactant conversions.

Details for Examples 14 and 15 are in Table 3.

TABLE 3

| Example | Catalyst Components | | | | | | Reaction Conditions | | Conversion (wt. %) | |
|---|---|---|---|---|---|---|---|---|---|---|
| | A | | B | | C | | | | | |
| | g | mmol | g | mmol | g | mmol | $H_2$ (psig) | °C. | DAB | COD |
| 14 | 0.049 | 0.080 | 0.056 | 0.20 | 0.082 | 0.48 | 16 | 60° | 33 | 76 |
| 15 | 0.049 | 0.080 | 0.056 | 0.20 | 0.082 | 0.48 | 50 | 60° | 37 | 78 |

Notes:
A = [RuCl$_2$(p-cymene)]$_2$
B = Tricyclohexylphosphine
C = 1,4-diacetoxy-2-butyne

EXAMPLES 16–17

Examples 16 and 17 were performed to demonstrate the effect of increased catalyst component (C), the carbon-to-carbon triple bond component.

The following procedure was employed. A solution was prepared consisting of [RuCl$_2$(p-cymene)]$_2$ (0.098 g , 0.16 mmol), tricyclohexylphosphine (0.090 g, 0.32 mmol), 1,4-diacetoxy-2-butyne (Aldrich), cis-1,4-DAB (7.4 mL, 47 mmol), 1,5-COD (30.0 mL, 244 mmol), and 10 mL chlorobenzene solvent in a 6-oz glass Fisher-Porter bottle under N$_2$ atmosphere (15 psia). The bottle was sealed and then immersed in a 60° C. oil bath and the sodium was magnetically stirred for several minutes to dissolve all the solids. The bottle was then pressurized to 15–20 psig with hydrogen gas (H$_2$). After pressurization, the bottle was sealed off under static hydrogen pressure (valve to hydrogen source was closed) and the solution was stirred for 4 hours (since hydrogen pressurization) at 60° C. The bottle was then cooled to room temperature and depressurized, and the solution was analyzed by FID GC to determine reactant conversions. Reaction data and reactant conversions are given in the following Table 4.

TABLE 4

| Example | Catalyst Components | | | | | | Reaction Conditions | | Conversion (wt. %) | |
|---|---|---|---|---|---|---|---|---|---|---|
| | A | | B | | C | | | | | |
| | g | mmol | g | mmol | g | mmol | $H_2$ (psig) | °C. | DAB | COD |
| 16 | 0.098 | 0.16 | 0.090 | 0.32 | 0.082 | 0.48 | 15 | 60 | 46 | 86 |
| 17 | 0.098 | 0.16 | 0.090 | 0.32 | 0.164 | 0.96 | 15 | 60 | 51 | 92 |

EXAMPLES 18–21

The following procedure was employed to demonstrate effect of reaction temperature. A solution was prepared consisting of [RuCl$_2$(p-cymene)]$_2$ (0.049 g, 0.80 mmol), tricyclohexylphosphine (0.056 g, 0.20 mmol), 1,4-diacetoxy-2-butyne (0.082 g, 0.48 mmol—Narchem Corp.), cis-1,4-DAB (7.4 mL, 47 mmol), 1,5-COD (30.0 mL, 244 mmol), and 10 mL chlorobenzene solvent in a 6-oz glass Fisher-Porter bottle under N$_2$ atmosphere (15 psia). The bottle was sealed and then immersed in an oil bath at the desired temperature, and the solution was magnetically stirred for several minutes to dissolve all the solids. The bottle was then pressurized to 15–20 psig with hydrogen gas (H$_2$). After pressurization, the bottle was sealed off under static hydrogen pressure (valve to hydrogen source was closed) and the solution was stirred for 4 hours (since hydrogen pressurization) at the desired reaction temperature (the temperature of the oil bath). The bottle was then cooled to room temperature and depressurized, and the solution was analyzed by FID GC to determine reactant conversions. Reaction data and reactant conversions are given in the following Table 5.

TABLE 5

| | Catalyst Components | | | | | | Reaction Conditions | | Conversion (wt. %) | |
|---|---|---|---|---|---|---|---|---|---|---|
| | A | | B | | C | | | | | |
| Example | g | mmol | g | mmol | g | mmol | $H_2$ (psig) | °C. | DAB | COD |
| 18 | 0.049 | 0.080 | 0.056 | 0.20 | 0.082 | 0.48 | 15 | 45 | 5 | 19 |
| 19 | 0.049 | 0.080 | 0.056 | 0.20 | 0.082 | 0.48 | 16 | 60 | 33 | 76 |
| 20 | 0.049 | 0.080 | 0.056 | 0.20 | 0.082 | 0.48 | 15 | 82 | 51 | 91 |
| 21 | 0.049 | 0.080 | 0.056 | 0.20 | 0.082 | 0.48 | 19 | 90 | 41 | 84 |

EXAMPLES 22–25

The following Examples were performed according to the procedure of Example 4, except that different ruthenium compounds (catalyst component A) are employed. These ruthenium compounds are all of the [RuCl$_2$(arene)]$_2$ structure, but employ arenes other than p-cymene.

[RuCl$_2$(arene)]$_2$ compounds were prepared by heating a suspension of [RuCl$_2$(P-cymene)]$_2$ in neat arene.

EXAMPLE 22

[RuCl$_2$(4-tert-butyltoluene)]$_2$ was prepared by refluxing a suspension of [RuCl$_2$(p-cymene)]$_2$ (3 g, Strem Chemicals) in 100 mL 4-tert-butyltoluene (Aldrich, 95%, b.p. 190° C.) for 2 hours under N$_2$. The solution was cooled. Solids were collected by filtration and washed with heptane. A 2-gram portion of the isolated solids was refluxed in 100 mL fresh 4-tert-butyltoluene for 6 hours under N$_2$. This solution was cooled and the solids were isolated by filtration. The solids were washed with heptane and dried in a vacuum oven at 70° C. Approximately 1.95 grams of red crystals were obtained. $^1$H NMR analysis of this product was consistent with the material being 91% pure [RuCl$_2$(4-tert-butyltoluene)]$_2$ with about 9% unreacted [RuCl$_2$(p-cymene)]$_2$. $^1$H NMR data for [RuCl$_2$(4-tert-butyltoluene)]$_2$ (CDCl$_3$ solvent): δ 1.40 (s, 9H), 2.11 (s, 3H), 5.3 (d, 2H), 5.8 (d, 2H).

EXAMPLE 23

[RuCl$_2$(1,3-diisopropylbenzene)]$_2$ was prepared by stirring a suspension of [RuCl$_2$(p-cymene)]$_2$ (3 g) in 100 mL 1,3-diisopropylbenzene (Aldrich, 96%) for a total of 8 hours at 190° C. under N$_2$. The solution was cooled. Solids were collected by filtration, washed with heptane, and dried in a vacuum oven at 70° C. Approximately 2.6 grams of light brown solid was obtained. $^1$H NMR analysis of this product was consistent with the material being 90+ % pure [RuCl$_2$(1,3-diisopropylbenzene)]$_2$ with a small amount of unreacted [RuCl$_2$(p-cymene)]$_2$. $^1$H NMR data for [RuCl$_2$(1,3-diisopropylbenzene)]$_2$ (CDCl$_3$ solvent): δ 1.27 (d, 12H), 2.95 (m, 2H), 5.23 (s, 1H), 5.4 (d, 2H), 5.7 (t, 1H).

EXAMPLE 24

[RuCl$_2$(1,4-diisopropylbenzene)]$_2$ was prepared by stirring a suspension of [RuCl$_2$(p-cymene)]$_2$ (3 g) in 100 mL 1,4-diisopropylbenzene (Aldrich, 97%) for 8 hours at 190° C. under N$_2$. The solution was cooled. Solids were collected by filtration, washed with heptane, and dried in a vacuum oven at 70° C. Approximately 2.95 grams of red solid was obtained. A 2.6-gram portion of the red solid was stirred at 190° C. in 100 mL fresh 1,4-diisopropylbenzene for 6 hours. After cooling, solids were collected by filtration, washed with heptane, and dried in a vacuum oven at 70° C. A red-brown solid product was obtained (2.5 grams). $^1$H NMR analysis of this product was consistent with the material being 90+ % pure [RuCl$_2$(1,4-diisopropylbenzene)]$_2$ with a small amount of unreacted [RuCl$_2$(p-cymene)]$_2$. $^1$H NMR data for [RuCl$_2$(1,4-diisopropylbenzene)]$_2$ (CDCl$_3$ solvent): δ 1.28 (d, 12H), 2.9 (m, 2H), 5.45 (s, 4H).

EXAMPLE 25

[RuCl$_2$(1,3,5-triisopropylbenzene)]$_2$ was prepared by stirring a suspension of [RuCl$_2$(P-cymene)]$_2$ (3 g) in 120 mL 1,3,5-triisopropylbenzene (Aldrich, 97%) for a total of 8 hours at 190° C. under N$_2$. The solution was cooled to room temperature and then placed in a refrigerator for 2–3 days. Solids were collected by cold filtration, washed with heptane, and dried in a vacuum oven at 70° C. A red-brown solid product was obtained (3.25 grams). $^1$H NMR analysis of this product was consistent with the material being 90+ % pure [RuCl$_2$(1,3,5-triisopropylbenzene)]$_2$ with a small amount of unreacted [RuCl$_2$(p-cymene)]$_2$. $^1$H NMR data for [RuCl$_2$(1,3,5-triisopropylbenzene)]$_2$ (CDCl$_3$ solvent): δ 1.3 (d, 18H), 3.1 (m, 3H), 5.2 (s, 3H).

The following procedure given was employed for the olefin metathesis reaction of 1,5-COD and cis-1,4-DAB.

A solution was prepared consisting of [RuCl$_2$(arene)]$_2$ (0.040 mmol), tricyclohexylphosphine (0.028 g, 0.10 mmol), 1,4-diacetoxy-2-butyne (0.041 g, 0.24 mmol), cis-1,4-DAB (7.4 mL, 47 mmol), 1,5-COD (30.0 mL, 244 mmol), and 10 mL chlorobenzene solvent in a 6-oz glass Fisher-Porter bottle under N$_2$ atmosphere (15 psia). The bottle was sealed and then immersed in a 60° C.-oil bath and the solution was magnetically stirred for several minutes to dissolve all the solids. The bottle was then pressurized to 15–17 psig with hydrogen gas (H$_2$). After pressurization, the bottle was sealed off under static hydrogen pressure (valve to hydrogen source was closed) and the solution was stirred for 4 hours (since hydrogen pressurization) at 60° C. The bottle was then cooled to room temperature and depressurized, and the solution was analyzed by FID GC to determine reactant conversions. Reaction data and reactant conversions are given in the following table:

TABLE 6

| | | Catalyst Components | | | | | Reaction Conditions | | Conversion (wt. %) | |
|---|---|---|---|---|---|---|---|---|---|---|
| | Arene in Catalyst | A | | B | | C | $H_2$ | | | |
| Example | Component A | g | mmol | g | mmol | g | mmol | (psig) | °C. | DAB | COD |
| 22 | 4-tert-Butyltoluene | 0.026 | 0.040 | 0.028 | 0.10 | 0.041 | 0.24 | 15–17 | 60 | 32 | 71 |
| 23 | 1,3-Diisopropylbenzene | 0.027 | 0.040 | 0.028 | 0.10 | 0.041 | 0.24 | 15–17 | 60 | 7 | 34 |
| 24 | 1,4-Diisopropylbenzene | 0.027 | 0.040 | 0.028 | 0.10 | 0.041 | 0.24 | 15–17 | 60 | 22 | 60 |
| 25 | 1,3,5–Triisopropylbenzene | 0.030 | 0.040 | 0.028 | 0.10 | 0.041 | 0.24 | 15–17 | 60 | 28 | 67 |

Notes:
A = [RuCl$_2$(arene)]$_2$
B = Tricyclohexylphosphine
C = 1,4-diacetoxy-2-butyne Thus, in view of the above, the invention concerns, in part, the following:

A ruthenium-based catalyst system for ring-opening metathesis polymerization of cyclic olefins, metathesis of acyclic olefins, acyclic diene metathesis polymerization, cross-metathesis of cyclic and acyclic olefins, ring-closing metathesis, metathesis depolymerization of unsaturated polymers and metathesis of functionalized olefins, wherein said catalyst system comprises a ruthenium compound (A), a phosphorus compound (B), and a compound (C) containing a carbon-to-carbon triple bond, wherein mole ratios of A:B:C expressed as compounds are in the range of about 1.0:0.01–100:0.01–100, said ruthenium compound (A) is a Ru(II), Ru(III), or Ru(IV) compound containing an anionic ligand (X) and optionally containing an arene ligand and optionally a phosphorus compound ligand;

provided that said phosphorus compound (B) is optional if said ruthenium compound (A) contains a phosphorus-containing ligand.

The above ruthenium-based catalyst system wherein said ruthenium compound (A) is represented by the formula $$[RuX_n(PR'_3)_q(arene)_p]_z$$

where n=2, 3, or 4; q=0, 1, 2, 3, or 4; p=0 or 1; and z=1 or 2.

The above ruthenium-based catalyst system wherein said mole ratios of A:B:C expressed as compounds are in the range of about 1.0:0.1–40:0.1–40 (or about 1.0:0.2–20:0.2–20).

The above ruthenium-based catalyst system wherein X is an aliphatic anionic ligand (e.g., containing up to 20 or up to 12 or up to 8 or up to 6 carbon atoms such as methyl, ethyl, propyl, isopropyl, butyl, or hexyl) or an aromatic anionic ligand (e.g., containing up to 20 or up to 12 or up to 8 or up to 6 carbon atoms such as phenyl or benzyl), or wherein X is halogen (F, Cl, Br, and I), hydroxide, or alkoxide (e.g., OR$^3$ wherein R$^3$ is selected from the group consisting of alkyl, cycloalkyl, aryl, and alkylaryl groups (e.g., of up to about 20 or up to about 12 or up to about 8 or up to about 6 carbon atoms)), or wherein X is selected from the group consisting of nitrate, nitrite, acetate, trifluoroacetate, acetylacetonate, hexafluoroacetylacetonate, and mixtures thereof.

The above ruthenium-based catalyst system wherein R' is selected from R and (OR) where each of the R groups are the same or are independently selected from the group consisting of hydrogen, alkyl, cycloalkyl, aryl and arylalkyl groups (e.g., each group of up to about 20 or up to about 12 or up to about 8 or up to about 6 carbon atoms), unsubstituted or substituted (e.g., wherein the substituents may be halogen (F, Cl, Br, and I), or alkyl or aryl groups (e.g., of up to about 20 or up to about 12 or up to about 8 or up to about 6 carbon atoms)); if R' is OR then R' and R are not hydrogen; and if R' is R then at least one R is not hydrogen.

The above ruthenium-based catalyst system wherein said arene ligand of said ruthenium compound (A) is selected from the group consisting of an unsubstituted aromatic ligand (e.g., of up to about 30 or about 20 or about 15 carbon atoms), a substituted aromatic ligand (e.g., of up to about 30 or about 20 or about 15 carbon atoms), and mixtures thereof, wherein the substituents of said substituted aromatic ligand of said arene group of said ruthenium compound (A) are selected from the group consisting of halogen (F, Cl, Br, and I), alkyl and aryl groups (e.g., groups of up to about 25 or about 20 or about 12 or about 8 carbon atoms), trialkylsilyl and triarylsilyl groups (e.g., groups of up to about 25 or about 20 or about 15 or about 8 carbon atoms), and mixtures thereof. The arene ligand may be selected from alkylbenzenes, polyalkylbenzenes, arylbenzenes, polyarylbenzenes, halobenzenes, haloalkylbenzenes, haloarylbenzenes, alkylnaphthalenes, arylnaphthalenes, polyalkylnaphthalenes, polyarylnaphthalenes, halonaphthalenes, haloalkylnaphthalenes, and haloarylnaphthalenes. The arene ligand may be selected from the group consisting of benzene, toluene, xylene, cumene, cymene, p-cymene, durene, trimethylsilylbenzene, 1,4-bis(trimethylsilyl) benzene, and naphthalene.

The above ruthenium-based catalyst system wherein said phosphorus compound (B) is selected from the group consisting of phosphine compounds and phosphite compounds of the formulae PR$_3$, P(OR)$_3$, PH$_2$R, PHRR$^1$, PRR$^1$R$^2$, and P(OR)(OR$^1$)(OR$^2$), wherein R, R$^1$ and R$^2$ are the same or are independently selected from the group consisting of unsubstituted and substituted alkyl, cycloalkyl, aryl and arylalkyl groups (e.g., groups of up to about 20 or about 12 or about 8 or about 6 carbon atoms), wherein the substituents may be halogen (F, Cl, Br, and I), alkyl or aryl moieties of up to 20 carbon atoms (preferably up to about 12 carbon atoms, more preferably up to about 8 carbon atoms, most preferably up to about 6 carbon atoms). Phosphorus compound (B) is preferably a phosphine compound, more preferably a C$_3$ to C$_8$ tri-alkyl or -cycloalkyl phosphine, e.g., selected from the group consisting of tricyclohexylphosphine, triisopropylphosphine, and tricyclopentylphosphine.

The above ruthenium-based catalyst system wherein said compound (C) is a substituted or unsubstituted alkyne (e.g., of up to about 20 or up to about 16 or up to about 12 or up to about 8 carbon atoms), or is selected from the group consisting of a terminal alkyne, an internal alkyne, an alkyne possessing one or more aliphatic, aromatic, halogen (F, Cl, Br, and I), ester, hydroxyl, ketone, aldehyde, ether, carboxyl, amide, anhydride, nitrile, silyl or amine groups, and mixtures thereof, or is preferably selected from the group consisting of acetylene, propyne, 1-butyne, 2-butyne, 1-pentyne, 2-pentyne, 1-hexyne, 2-hexyne, 3-hexyne, 1-heptyne, 1-octyne, 1-decyne, 1-dodecyne, trimethylsilylacetylene, phenylacetylene, diphenylacetylene, 2-butyne-1,4-diol, ester derivatives of 2-butyne-1,4-diol such as 1,4-diacetoxy-2-butyne, 2-butyne-1,4-diol monoacetate, 2-butyne-1,4-diol diacetate, 2-butyne-1,4-diol monopropionate, 2-butyne-1,4-diol dipropionate, 2-butyne-1,4-diol monobenzoate, and 2-butyne-1,4-diol dibenzoate.

The above ruthenium-based catalyst system wherein hydrogen ($H_2$) is present as a catalyst system activator at a partial pressure of hydrogen of from $1\times 10^{-2}$ mm Hg to about 200 atmospheres (or 0.1 mm Hg to about 100 atmospheres or 1 mm Hg to about 20 atmospheres).

The above ruthenium-based catalyst system wherein said ruthenium compound (A) is selected from the group consisting of $[RuCl_2(p\text{-cymene})]_2$, $[RuCl_2(4\text{-tert-butyltoluene})]_2$, $[RuCl_2(1,3\text{-diisopropylbenzene})]_2$, $[RuCl_2(1,4\text{-diisopropylbenzene})]_2$, and $[RuCl_2(1,3,5\text{-triisopropylbenzene})]_2$, said phosphorus compound (B) is tricyclohexylphosphine, and said compound containing a carbon-to-carbon triple bond (C) is selected from the group consisting of 1,4-diacetoxy-2-butyne, 3-hexyne, and 1-decyne.

The above ruthenium-based catalyst system wherein said ruthenium compound (A) is selected from the group consisting of $[RuX_2(arene)]_2$, $RuX_2(arene)(PRR^1R^2)$, $RuX_2(arene)(PHRR^1)$, $RuX_2(arene)(PH_2R)$, $RuX_2(arene)[P(OR)(OR^1)(OR^2)]$, $RuX_3$, $RuX_3$-hydrate, $RuX_2(PRR^1R^2)_3$, $RuX_2(PHRR^1)_3$, $RuX_2(PH_2R)_3$, $RuX_2[P(OR)(OR^1)(OR^2)]_3$, $RuX_2(PRR^1R^2)_4$, $RuX_2(PHRR^1)_4$, $RuX_2(PH_2R)_4$, and $RuX_2[P(OR)(OR^1)(OR^2)]_4$, wherein P is phosphorus, X is selected from the group consisting of an aliphatic anionic ligand, an aromatic anionic ligand, halogen (F, Cl, Br, and I), hydroxide, alkoxide, nitrate, nitrite, acetate, trifluoroacetate, acetylacetonate, hexafluoroacetylacetonate, and mixtures thereof, wherein R, $R^1$ and $R^2$ are the same or are independently selected from the group consisting of unsubstituted and substituted alkyl, cycloalkyl, aryl, and arylalkyl groups, wherein the arene group of said ruthenium compound (A) is selected from the group consisting of an unsubstituted aromatic ligand, a substituted aromatic ligand, and mixtures thereof.

A process for olefin metathesis in the presence of a catalyst system for ring-opening metathesis polymerization of cyclic olefins, metathesis of acyclic olefins, acyclic diene metathesis polymerization, cross-metathesis of cyclic and acyclic olefins, ring-closing metathesis, metathesis depolymerization of unsaturated polymers and metathesis of functionalized olefins, said process comprising contacting at least one olefin with the catalyst system described above.

The above process wherein hydrogen is present as a catalyst system activator at a partial pressure of hydrogen of from $1\times 10^{-2}$ mm Hg to about 200 atmospheres (or 0.1 mm Hg to about 100 atmospheres or 1 mm Hg to about 20 atmospheres).

The above process wherein said process is conducted at a temperature within a range of from about 0° C. to about 250° C. (or from about 0° C. to about 200° C. or from about 0° C. to about 150° C.).

The above process wherein said process is conducted at a pressure of from about $1\times 10^{-2}$ mm Hg to 200 atmospheres (or at a pressure of from about 0.1 mm Hg to 100 atmospheres or at a pressure of from about 1 mm Hg to 20 atmospheres).

The above process wherein said ruthenium compound (A) is selected from the group consisting of $[RuCl_2(p\text{-cymene})]_2$, $[RuCl_2(4\text{-tert-butyltoluene})]_2$, $[RuCl_2(1,3\text{-diisopropylbenzene})]_2$, $[RuCl_2(1,4\text{-diisopropylbenzene})]_2$, and $[RuCl_2(1,3,5\text{-triisopropylbenzene})]_2$, said phosphorus compound (B) is tricyclohexylphosphine, and said compound containing a carbon-to-carbon triple bond (C) is selected from the group consisting of 1,4-diacetoxy-2-butyne, 3-hexyne, and 1-decyne.

The above process of wherein mole ratios of A:B:C, present in said catalyst system, expressed as compounds, are in the range of 1.0:0.01–100:0.01–100 (or are in the range of 1.0:0.1–40:0.1–40 or are in the range of 1.0:0.2–20:0.2–20).

The above process comprising reacting cis,cis-1,5-cyclooctadiene and cis-1,4-diacetoxy-2-butene with said catalyst system to yield acetate-terminated 1,4-polybutadiene or reacting cis,cis-1,5-cyclooctadiene with said catalyst system to yield 1,4-polybutadiene.

Any product or process described herein.

The use of the catalyst system described above for ring-opening metathesis polymerization of cyclic olefins, metathesis of acyclic olefins, acyclic diene metathesis polymerization, cross-metathesis of cyclic and acyclic olefins, ring-closing metathesis, metathesis depolymerization of unsaturated polymers and metathesis of functionalized olefins.

The use of the catalyst system described above for the manufacture of monofunctional polymers (average functionality number of 0.7 as determined by nuclear magnetic resonance spectroscopy ($^{13}C$ NMR) and telechelic difunctional polymers (average functionality number of 1.7 as determined by nuclear magnetic resonance spectroscopy ($^{13}C$ NMR)).

A catalyst system useful in olefin metathesis reactions comprising a reaction product of a ruthenium compound, a phosphorus-containing compound, and a compound containing a carbon-carbon triple bond. The catalyst system wherein the phosphorus-containing compound is a phosphine which may be included within said ruthenium compound.

The following U.S. Patents are incorporated herein by reference in their entirety: U.S. Pat. Nos. 5,403,904; 5,519,101; 5,512,635; 5,559,190; 5,589,548; 5,589,543. The following U.S. Patent Applications are incorporated herein by reference in their entirety: U.S. patent application Ser. Nos. 08/543,080 filed on Oct. 13, 1995 now U.S. Pat. No. 5,621,047; 08/706,893 filed on Sep. 3, 1996, now U.S. Pat. No. 5,731,383.

Further variations and modifications of the invention will become apparent to those skilled in the art from the foregoing and are intended to be encompassed by the claims appended hereto.

That which is claimed is:

1. A ruthenium-containing olefin metathesis catalyst system comprising a reaction product of a ruthenium compound (A), a phosphorus compound (B), and a compound (C) containing a carbon-to-carbon triple bond, in the presence of an olefin to be metathesized and hydrogen, wherein mole ratios of compounds A:B:C are in the range of about 1.0:0.01–100:0.01–100, wherein hydrogen is present as a catalyst system activator at a partial pressure of hydrogen of from $1\times 10^{-2}$ mm to about 200 atmospheres;

wherein said ruthenium compound (A) is selected from the group consisting of [RuX$_2$(arene)]$_2$, RuX$_2$(arene)(PRR$^1$R$^2$), RuX$_2$(arene)(PHRR$^1$), RuX$_2$(arene)(PH$_2$R), RuX$_2$(arene)[P(OR)(OR$^1$)(OR$^2$)], RuX$_3$, RuX$_3$-hydrate, RuX$_2$(PRR$^1$R$^2$)$_3$, RuX$_2$(PHRR$^1$)$_3$, RuX$_2$(PH$_2$R)$_3$, RuX$_2$[P(OR)(OR$^1$)(OR$^2$)]$_3$, RuX$_2$(PRR$^1$R$^2$)$_4$, RuX$_2$(PHRR$^1$)$_4$, RuX$_2$(PH$_2$R)$_4$, and RuX$_2$[P(OR)(OR$^1$)(OR$^2$)]$_4$, wherein P is phosphorus, and wherein R, R$^1$ and R$^2$ are the same or different and are each selected from the group consisting of unsubstituted and substituted alkyl, cycloalkyl, aryl and arylalkyl groups of up to about 20 carbon atoms; and wherein (X) comprises an aliphatic or aromatic anionic ligand containing up to 20 carbon atoms or halogen, nitrate, nitrite, hydroxide or alkoxide having the formula OR$^3$ and wherein R$^3$ is selected from the group consisting of alkyl, cycloalkyl, aryl, and alkylaryl groups of up to 20 carbon atoms and wherein the arene ligand is selected from the group consisting of an unsubstituted aromatic ligand, a substituted aromatic ligand and mixtures thereof;

provided that said phosphorus compound (B) is optional if said ruthenium compound (A) contains said optional phosphorus compound as a ligand.

2. The ruthenium-containing catalyst system of claim 1, wherein said compound (C) is selected from the group consisting of a terminal alkyne, an internal alkyne, an alkyne possessing one or more aliphatic, aromatic, halogen, ester, hydroxyl, ketone, aldehyde, ether, carboxyl, amide, anhydride, nitrile, silyl or amine groups, and mixtures thereof.

3. The ruthenium-containing catalyst system of claim 2, wherein said compound (C) is selected from the group consisting of acetylene, propyne, 1-butyne, 2-butyne, 1-pentyne, 2-pentyne, 1-hexyne, 2-hexyne, 3-hexyne, 1-heptyne, 1-octyne, 1-decyne, 1-dodecyne, trimethylsilyacetylene, phenylacetylene, diphenylacetylene, 2-butyne-1,4-diol, 1,4-diacetoxy-2-butyne, 2-butyne-1,4-diol monoacetate, 2-butyne-1,4-diol diacetate, 2-butyne-1,4-diol monopropionate, 2-butyne-1,4-diol dipropionate, 2-butyne-1,4-diol monobenzoate, and 2-butyne-1,4-diol dibenzoate.

4. The ruthenium-containing catalyst system of claim 1, wherein said compound (C) is a substituted or unsubstituted alkyne.

5. The ruthenium-containing catalyst system of claim 4, wherein said compound (C) is an alkyne of up to about 20 carbon atoms.

6. The ruthenium-containing catalyst system of claim 1, wherein said phosphorus compound (B) is selected from the group consisting of tricyclohexylphosphine, triisopropylphosphine, and tricyclopentylphosphine.

7. The ruthenium-containing catalyst system of claim 1, wherein said phosphorus compound (B) is selected from the group consisting of phosphine compounds and phosphite compounds of the formulae PR$_3$, P(OR)$_3$, PH$_2$R, PHRR$^1$, PRR$^1$R$^2$, and P(OR)(OR$^1$)(OR$^2$), wherein R, R$^1$ and R$^2$ are the same or different and are each selected from the group consisting of unsubstituted and substituted alkyl, cycloalkyl, aryl and arylalkyl groups.

8. The ruthenium-containing catalyst system of claim 7, wherein said phosphorus compound (B) is selected from the group consisting of phosphine compounds and phosphite compounds of the formulae PR$_3$, P(OR)$_3$, PH$_2$R, PHRR$^1$, PRR$^1$,R$^2$, and P(OR)OR$^1$)(OR$^2$), wherein R, R$^1$ and R$^2$ are the same or different and are each selected from the group consisting of unsubstituted and substituted alkyl, cycloalkyl, aryl and arylalkyl groups of up to about 20 carbon atoms.

9. The ruthenium-containing catalyst system of claim 1, wherein said ruthenium compound (A) is selected from the group consisting of [RuCl$_2$(p-cymene)]$_2$, [RuCl$_2$(4-tert-butyltoluene)]$_2$, [RuCl$_2$(1,3-diisopropylbenzene)]$_2$, [RuCl$_2$(1,4-diisopropylbenzene)]$_2$, and [RuCl$_2$(1,3,5-triisopropylbenzene)]$_2$, said phosphorus compound (B) is tricyclohexylphosphine, and said compound containing a carbon-to-carbon triple bond (C) is selected from the group consisting of 1,4-diacetoxy-2-butyne, 3-hexyne, and 1-decyne.

10. The ruthenium-containing catalyst system of claim 1, wherein said arene ligand of said ruthenium compound (A) is selected from the group consisting of benzene, toluene, xylene, cumene, cymene, p-cymene, durene, trimethylsilylbenzene, 1,4-bis(trimethylsilyl) benzene, and naphthalene.

11. The ruthenium-containing catalyst system of claim 1, wherein said arene ligand of said ruthenium compound (A) is selected from the group consisting of alkylbenzenes, polyalkylbenzenes, arylbenzenes, polyarylbenzenes, halobenzenes, haloalkylbenzenes, haloarylbenzenes, alkylnaphthalenes, arylnaphthalenes, polyalkylnaphthalenes, polyarylnaphthalenes, halonaphthalenes, haloalkylnaphthalenes, and haloarylnaphthalenes.

12. The ruthenium-containing catalyst system of claim 1, wherein said arene ligand of said ruthenium compound (A) is selected from the group consisting of an unsubstituted aromatic ligand of up to about 30 carbon atoms, a substituted aromatic ligand of up to about 30 carbon atoms, and mixtures thereof.

13. The ruthenium-containing catalyst system of claim 12, wherein the substituents of said substituted aromatic ligand are selected from the group consisting of halogen, alkyl, aryl, trialkylsilyl, and triarylsilyl groups, and mixtures thereof.

14. The ruthenium-containing catalyst system of claim 13, wherein said substituents of said substituted aromatic ligand are selected from the group consisting of halogen, alkyl and aryl groups of up to 25 carbon atoms, trialkylsilyl and triarylsilyl groups of up to 25 carbon atoms, and mixtures thereof.

* * * * *